United States Patent [19]

Ramos Martinez

[11] Patent Number: 5,074,858
[45] Date of Patent: Dec. 24, 1991

[54] SUPPORT FOR IMPLANTATION OF CARDIAC VALVULAR PROSTHESES

[76] Inventor: Wilson Ramos Martinez, Doctor Fleming, 24, Madrid, Spain

[21] Appl. No.: 470,973

[22] Filed: Jan. 26, 1990

[30] Foreign Application Priority Data

Oct. 3, 1989 [ES] Spain .................................. 8903326

[51] Int. Cl.⁵ .............................................. A61F 2/24
[52] U.S. Cl. ........................................ 606/1; 606/148; 623/2; 248/229
[58] Field of Search ............... 623/2; 606/1, 144, 148, 606/150; 248/229, 278, 279

[56] References Cited

U.S. PATENT DOCUMENTS 3,221,743 12/1965 Thompson et al. ...................... 606/1
4,878,494 11/1989 Phillips et al. ............................ 623/2

*Primary Examiner*—Stephen C. Pellegrino
*Assistant Examiner*—Michael Rafa
*Attorney, Agent, or Firm*—Darby & Darby

[57] ABSTRACT

The support consists of an architectural functional unit made up of modules articulable in such a way that the unit is to be fixed to one of the branches of the sternal separator which is placed in the patient. Structurally the support includes a section (1) for securing the sternal separator from whose section a first module made up of a tube (3) and a telescopic rod (4) immovable by a radial screw (5) emerges. This module is followed by another one made up of a tube (7) joined to the end of the rod (4), tube which is a rotation support for a fourchet (8) to whose side branches grooved sections (9) through which grounds of suture thread (23) pass are fixed. The ends of the fourchet (8) bear a rotating tube in which a rod (15) to which the prosthesis itself (17) is secured is mounted in an inclined manner and a middle piece (18) is inserted.

6 Claims, 4 Drawing Sheets

SUPPORT FOR IMPLANTATION OF CARDIAC VALVULAR PROSTHESES

OBJECT OF THE INVENTION

As is expressed in the title of this specification, the present invention refers to a support for implantation of cardiac valvular prostheses, which support is to be secured on one of the branches corresponding to the sternal separator of the patient. The support itself is made up of several elements or modules capable of rotating and tilting among each other in order to orient the prosthesis to be implanted at any height and in any position. The prosthesis is secured in the end of a rod which forms part of the support unit.

Independent of the services and advantages that the support offers and which will be put forth in full detail throughout the present description, it can be said that it is a mechanical element which substitutes with absolute guarantees and even with much more efficiency one of the assistant surgeons who are required in operations in which cardiac valvular prostheses are implanted.

BACKGROUND OF THE INVENTION

The implantation of cardiac valvular prostheses, mechanical as well as biological type ones, requires a very perfected technique and a specific procedure so that aside from the main surgeon two assistant heart surgeons are needed in order to be able to adequately implant the prosthesis.

In the process that is carried out on the patient the main surgeon first proceeds to stitch the patient's valvular cardiac ring and then he passes the needle and suture thread through the Teflon which forms the securing ring of the prosthesis which is going to be implanted.

This prosthesis must be held during the entire process by an assistant surgeon who cannot do anything else. Therefore, one surgeon spends all the time dedicated to this surgical step, since aside from holding the prosthesis in a suitable position he must also place the suture threads in the correct position so that they do not get tangled and bother the main surgeon, hampering the process.

On the other hand, in the processes of implantation of a mitral prosthesis, the matter becomes complicated since two assistants are necessary. One of them must keep the separator of the left auricle in the correct position so that the main surgeon can operate with a good view and a good surgical field upon the mitral valve and all of its surroundings, seeing all of the auricular structures well which is of the utmost importance in this process.

It is unquestionable that the present system which is none other than the one described, entails a series of inconveniences which can be summarized as the following:

1. At least two assistant surgeons are needed, aside from the main surgeon in order to be able to efficiently effect the implantation process.

2. The assistant surgeon handles the prosthesis and this means that there is a potential risk of asepsis of the prosthesis (a fact of the utmost importance, as one can easily assume.) The surgeon may have worked with a ripped glove though it is in a single surgical step.

3. The main surgeon does not have a good panoramic view of the development of the process since his field of vision is hampered by the assistant surgeon's hands, thus he cannot adequately evaluate the orientation or spatial arrangement of the suture threads.

4. The assistant surgeon cannot remain with the prosthesis in a motionless state since he has nowhere to rest his hand and this causes the spatial plane of the prosthesis held by the assistant surgeon and exposed to the main surgeon to vary constantly. The main surgeon is even distracted and losses time and concentration in the development of the process.

5. The assistant surgeon, due to the above reason, cannot do anything else during the process such as aspirate, cut threads, help separate structures for the main surgeon at a specific moment when he were to need it, etc.

DESCRIPTION OF THE INVENTION

On the basis of the stated circumstances and inconveniences, the applicant as a professional in this field has conceived a support for securing the cardiac valvular prosthesis during the process of implantation thereof in a patient, a support which solves all the above cited problems and also offers a series of advantages that lead to an enormously advantageous action with regard to the process of implantation of cardiac valvular prosthesis over what is presently used.

The support in question consists of several modules articulable among each other, forming a single functional and architectural unit, so that the considered first module comprises a "C" section which is complemented by a transversal screw mounted on the top branch, so that through the "C" section and in collaboration with the screw, the unit is secured on the respective branch of the sternal separator, simply by placing the branch of the sternal separator between the two branches of the "C" section which forms the module or securing base of the support and by means of the screw to effect the tightening and respective immobilization.

The second module is comprised of a pair of telescopic tubes which vertically emerge from the top branch of the securing "C" section. The outside tube is linked to this branch, while the inside tube moves and rotates with regard to the former. It can be secured in any position by means of a radial screw.

A second tube on which the transversal branch of a "U" section which can rotate around said tube, or what is the same tilt practically 360° is linked transversally on the top end of the displaceable and rotating tube or rod. Likewise, it is set in any position by means of another radial screw.

The branches of the cited "U" section run according to two paths, one considered as ascending corresponding to a first section of these branches and another considered as horizontal and which determines the end section of the same. It is provided that the ends of these two branches are linked to a pair of fixed ferrules among which a new tube likewise capable of rotating 360° is mounted and whose tube can also be secured in any position by means of a side screw.

This third tube has transversally and in the center a hole for the passing of a rod which is going to hold the cardiac valvular prosthesis itself. This rod is capable of moving axially in the hole so that the prosthesis can be located at a higher or lower height and since the cylinder rotates, the prosthesis, as has been said, can also be oriented in any direction, with the particular feature that this rod holding the prosthesis is immobilized by means of a side screw axial to the cylinder itself.

The unit is complemented by two conduits or grooved section which run toward the part considered as the rear with a slight descending incline and with a slight divergence. The conduits have an end superposed to the ferrules for mounting the cylinder holding the rod which secures the prosthesis, while the other end of these conduits expand so that through the same the suture threads which come from the securing ring of the prosthesis and previously from the patient's implantation ring drop. Thus these suture threads will always remain duly oriented and positioned without being any obstacle for the main surgeon and without tangling together, since upon coming out of the conduits the cited suture threads are secured by some clamp type clips and inasmuch as in implantations of cardiac valvular prosthesis three groups of four pairs of suture threads in each group are required, two of these groups run through the conduits and each one of them will be secured where it comes out by means of the corresponding clamp or clip, while the third group of suture threads remains oriented in front of the surgical area or field itself, and this is also secured by another clamp or clip.

On the other hand, the prosthesis securing rod has in its bottom end a threaded portion for coupling to a hole likewise threaded and corresponding to a so-called "connection" piece which is precisely the one which is going to support the prosthesis by means of the so-called "rotator", an element which has a part in which precisely the complementary middle securing piece couples.

Inasmuch as presently there are five types of mechanical prostheses and two types of biological prostheses, several other variants of said middle coupling piece will be required, in other words, the one that is mounted between the rod and the rotator of the prosthesis in such a way that in these variants only the diameter of the thread which precisely couples the rotator changes.

The support described and made in accordance with the object of the invention offers the following advantages:

1st. Fewer hands are needed and thus at least one assistant surgeon can be eliminated.

2nd. The operating time of the process is reduced to the maximum since the main surgeon depends only upon his efficiency and ability to carry out the process in the minimum time possible. Most of the time this is vital, and many risks of long operations are eliminated.

3rd. It eliminates the possibility that the main surgeon orient the valvular prosthesis to be implanted in a position opposite to the correct one and carries out the process backwards, without realizing it, which is what would happen and what has happened sometimes.

Upon keeping the prosthesis in a static firm position with an excellent spatial projection, the main surgeon and the assistant surgeon are constantly seeing the situation of the entire system: the patient's valvular ring and the situation of the suture threads in the same; the valvular prosthesis to be implanted and the situation of the suture threads in the entire contour of the Teflon which comprises its securing ring; instant spatial visualization and situation. Even the prosthesis can be rotated to see its entire circumference and to see whether the suture threads have become tangled which could happen and which notably complicates the process lossing a lot of time which, on occasions can be very important for the patient.

4th. Once the main surgeon has effected the two suture movements, in other words, on the patient's valvular ring and the valvular prosthesis which is going to be implanted, the suture threads rest on the grooved surfaces of the support, which prevents said threads from becoming tangled together and from falling and hampering the main surgeon's visual field upon the surgical field he is operating on. Besides said threads are kept from the patient's valvular ring to the prosthesis under strain, modifying the same in the degree that the main surgeon himself desires for his own convenience, in such a way that in all this operating time the main surgeon works alone without any type of problem.

5th. The support in question can be used for all types of implantations of cardiac valvular prostheses, mitral as well as aortic or tricuspid ones.

6th. The possibility of tilting and rotating all the elements which form the apparatus, the prosthesis can be situated with any orientation and at any height in no more than ten seconds which is the time needed to screw the corresponding tightening screws.

To all of these advantages logically the absence of "surgical handling" of the prosthesis by the assistant surgeon and by the main surgeon himself must be added, as well as the elimination of possible "dislocations" (above all in the variety of biological prostheses whose structures are very fragile) of the elements comprising the prosthesis, since the same is not touched at all with the support of the invention.

In short, it comprises a modular support articulable in a single unit, offering invaluable help to the surgeon in cardiac valvular prostheses implantation operations, in such a way that with its combined movements of tilting and rotation of the distant parts or elements which comprise it, it is possible to attain the desired arrangement for direct and rapid assistance of the surgeon, favoring his services to the maximum and acting as a true assistant heart surgeon.

In order to complement the description which is going to be made hereafter and for the purpose of helping to provide a better understanding of the features of the invention, the present specification is accompanied by a set of drawings on the basis of whose figures the extent and true object of the invention will be more easily understood.

DESCRIPTION OF THE PREFERRED EMBODIMENT

Figure 1:
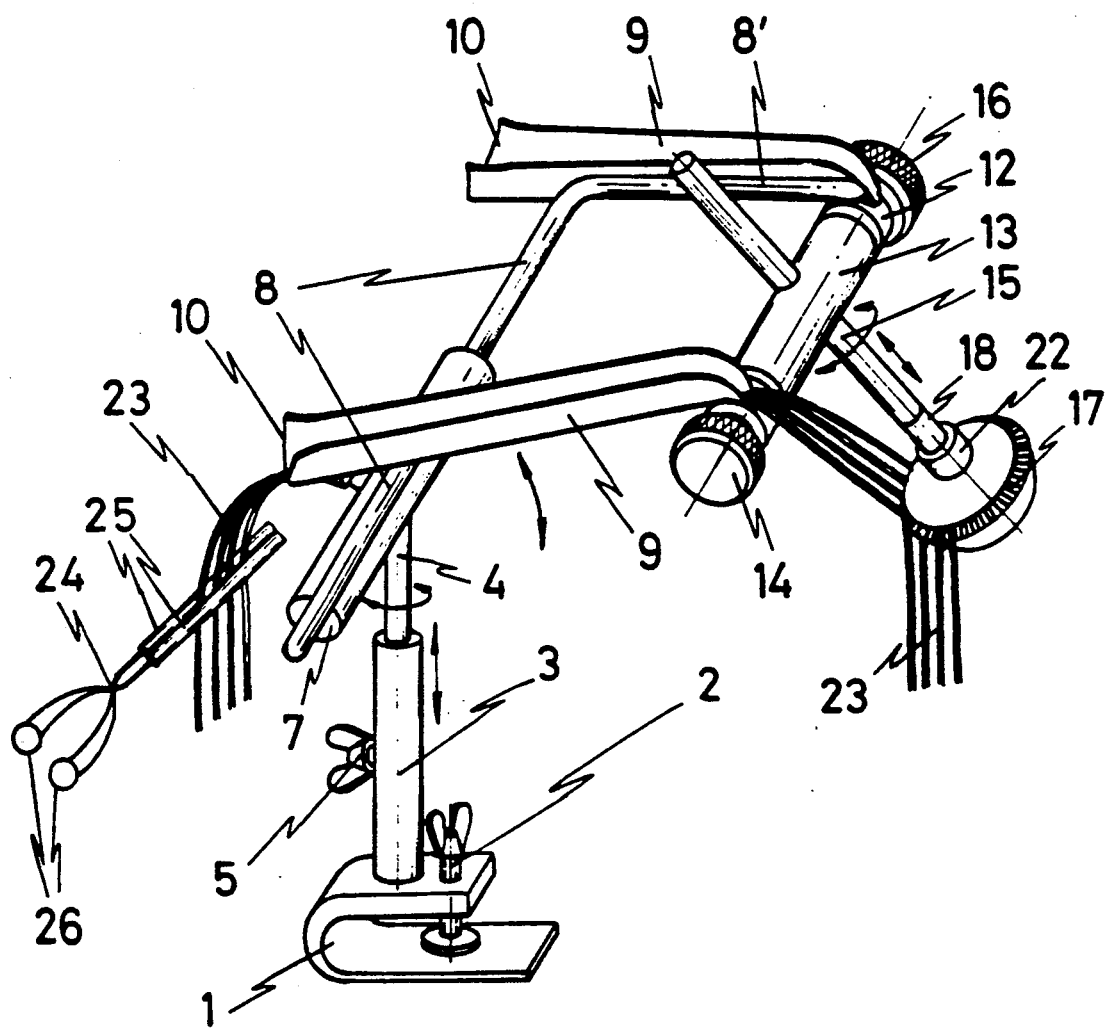
FIG. 1. It shows a general perspective view of the support for implantation of cardiac valvular prostheses made in accordance with the object of the invention.

In view of the mentioned figures, it can be observed how the support object of the invention is formed by a series of elements or modules articulated among each other, in such a way that the unit is to be secured to one of the branches of the sternal separator which is mounted on the patient, securing which is done by means of a "C" section 1 whose bottom branch is longer than the top one and narrower than the latter in such a way that between these two branches of section 1 the branch corresponding to the sternal separator will remain. It is secured to this by means of a pressure screw 2 mounted through the top branch of the section 1 itself, as is clearly shown in FIG. 1.

A fixed tube 3 on which a tube or rod 4 which can be immobilized in any position by means of a radial screw 5 placed upon the tube itself 3 is displaceably mounted in an ascending and descending direction emerges vertically upward from the top branch of section 1. In FIG. 2 one can see in full detail the tube 3 linked to the top part of the branch corresponding to section 1, a tube which continues in a hole 6 provided precisely in the top branch of section 1, while the tube or rod 4, telescopically displaceable in the inside of the tube 3, ends in the top part in a transversal and horizontal cylinder 7 in which a fourchet 8 formed by a rod or similar element with its transversal branch placed precisely in the inside of the tube 7 is situated rotatably or tiltably, while its side branches project in an ascending manner and subsequently it bends and determines practically horizontal sections 8' upon whose sections respective grooved sections 9 are collaterally linked, as is observed in FIG. 3, with the particular feature that these channels 9 are oriented with a slight divergence and incline descending towards the rear part of the support unit, and determining a broadening of the opening of the channel, according to reference 10 in that end towards which they diverge, as is observed in FIG. 1.

The fourchet 8, as was said, can tilt or rotate 360° with regard to the tube 7 on which it is mounted, locking in any position by means of a screw 11 mounted radially on the tube 7, as is also shown in FIG. 2.

Figure 3:
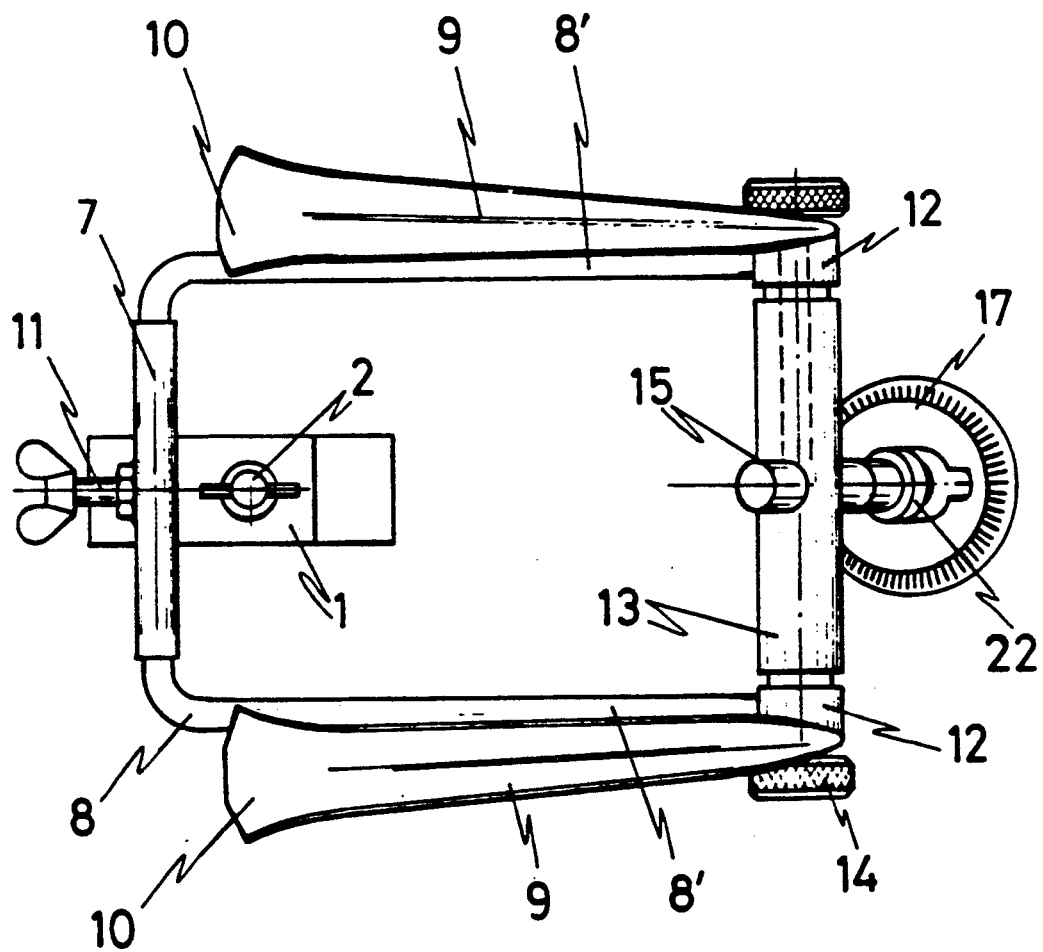
FIG. 3. It shows a top view of the support unit represented in FIG. 1, allowing one to observe the shape and divergence of the conduits.
Figure 4:
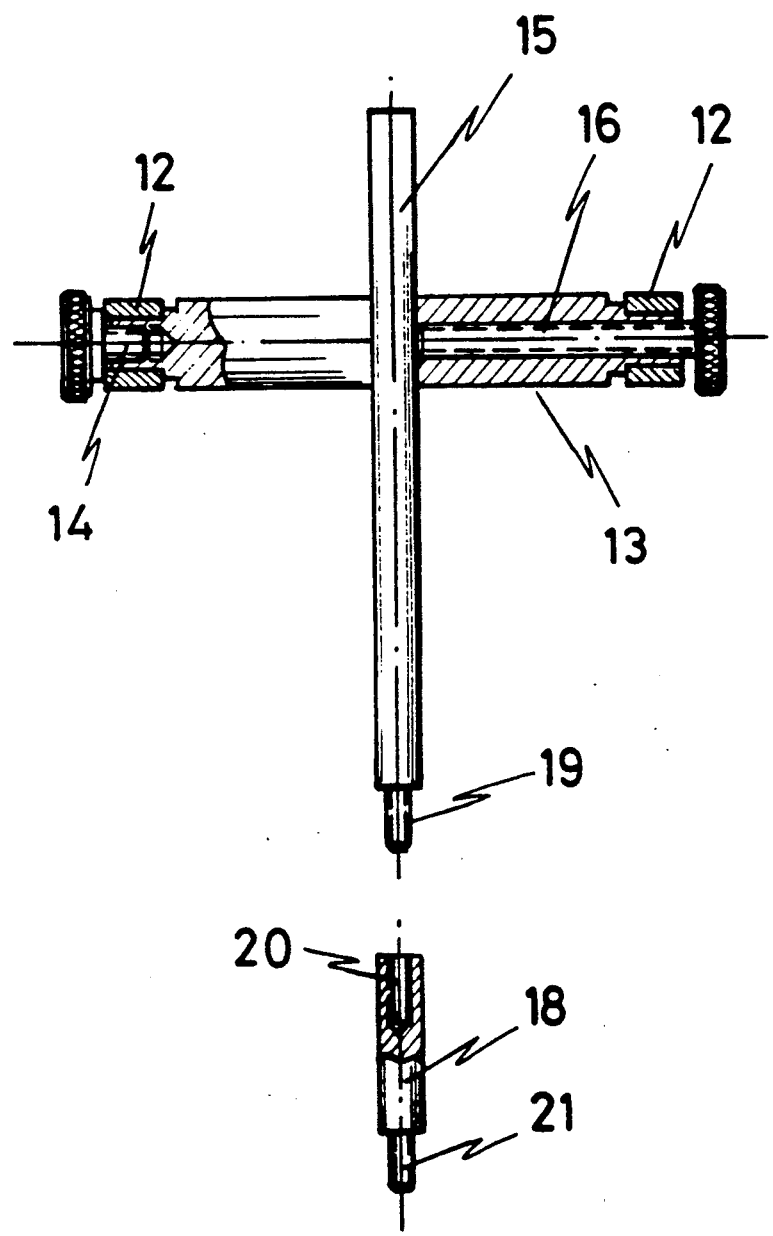
FIG. 4. It shows another detailed view of the securing rod of the prosthesis to be implanted with the middle piece to which the rotator of the prosthesis itself is secured. The rod is mounted through and transversally to a roller rotating around some ferrules functioning as a support, with locking elements of the roller itself and immobilization of said rod.

The ends of the branches 8' corresponding to the fourchet 8 are linked to the respective pieces 12 forming both ferrules between which a new tube or cylinder 13 which rotates on that assembly on the end ferrules 12 is mounted, also with the particular feature that upon said pieces or ferrules 12 the initial ends corresponding to the grooved sections 9 are mounted and adapted as is clearly shown in FIG. 3.

As has been said, this roller or cylinder 13 rotates in its assembly on the ferrules 12 and can be locked by means of a side axial screw 14 provided in one of the ends.

On the other hand, said cylinder or tube 13 is affected by a transversal hole in which a rod 15 which is going to be precisely what secures the cardiac valvular prosthesis is situated. The rod rotates in its assembly upon the hole of the cylinder or ferrules 13 and it can be immobilized by a side screw 16 in opposition to the lock screw 14 of the cylinder or roller 13.

Figure 2:
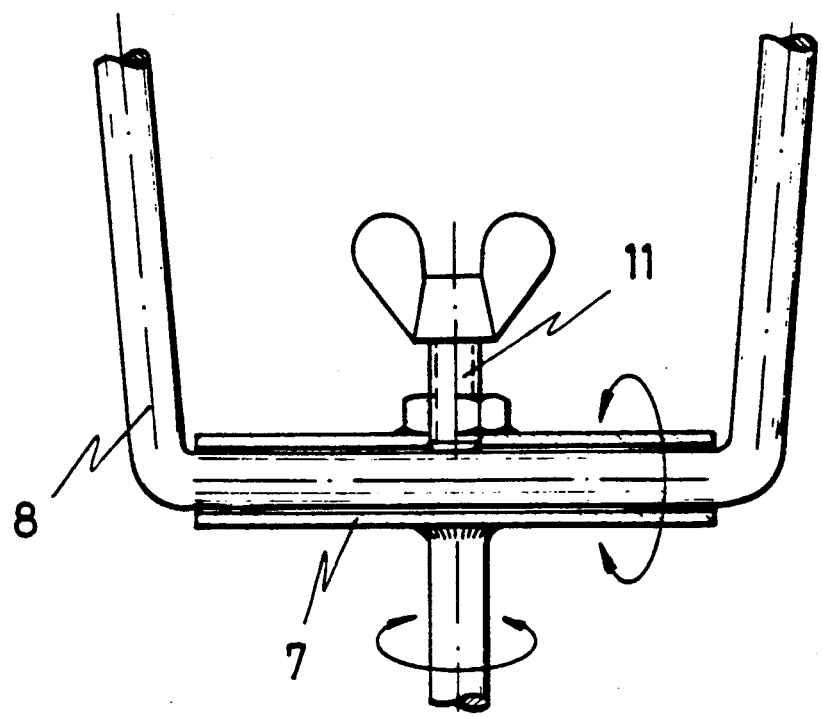
FIG. 2. It shows a detailed view corresponding to a raised sectional view of the tube that is linked and which emerges from the top branch of the securing base, containing inside it the telescopically displaceable tube or rod which has in its top end the tube around which the element comprising the fourchet to which the side conduits are linked is mounted rotatably. The radial lock screws of the moveable elements are observed in these figures.
Figure 2:
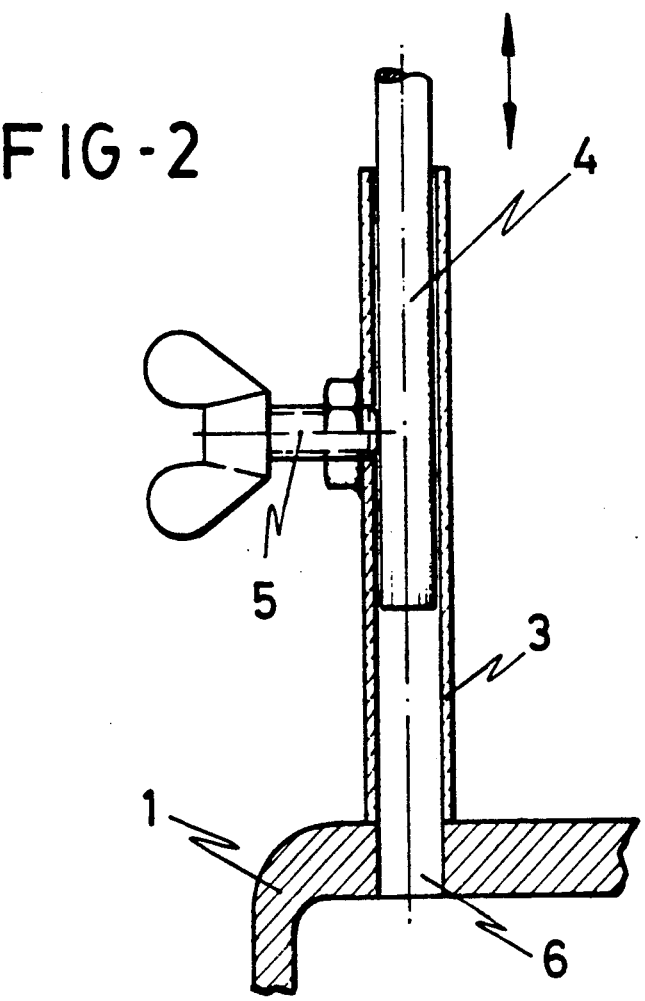

The securing of the prosthesis itself 17, shown in FIG. 1 with its prosthesis securing ring, is done by means of a middle piece 18 capable of coupling and uncoupling the rod 15 for which purpose the rod has in its end a threaded section 19 capable of coupling in a complementary hole also threaded 20 provided for this purpose in one of the ends of piece 18, which has the same shape as the rod 15 although it is much shorter.

This middle or coupling piece 18 has in its end opposite the one of the threaded hole 20, an extension 21 also threaded for the securing of the corresponding rotator 22 connected to to the prosthesis itself 17, in such a way that inasmuch as different types of prosthesis exist, some other pieces 18 will be required. All of them will be identical except in the diameter of the threaded extension 21 so that they can adapt to the different measurements that the different types of prosthesis have, or what is the same, the different types of rotators for said prosthesis.

In accordance with this structure and arrangement of the elements, the support is capable of reaching a higher or lower height in accordance with the telescopic nature of the tube or rod 4 in its variable mounting on the tube 3. Likewise the unit can vary in orientation in the first place due to the rotation of the fourchet 8 regarding the tube 7 on which it is mounted. Besides it is possible to also vary the orientation in the direction of rotation and ascent and descent of the prosthesis itself 17 in its assembly on tube or cylinder 13, which rotates on itself. Besides, the prosthesis 17 in its assembly on the rod 15 can also rise and descend, even rotate, as it has been said, as a result of rod 15 being displaceable and immobilizable in its arrangement on the tube or roller 13.

Therefore, the unit can vary in orientation, height, etc. which permits the surgeon to carry out the process in the desired form with total convenience.

As is normal in cardiac valvular implants, the securing of the same is done by means of suture threads. There are three groups of suture threads 23 which, coming from the patient's valvular ring, will logically pass through the securing ring 17 of the prosthesis.

There are three groups of suture threads, each group comprising four pairs of threads, in such a way that two of them are channeled in sections 9, hanging through the widened ends 10 of the grooved sections 9 and held in each case by a clip type clamp 24, which is logically formed by two branches provided with both tubes 25 which are the ones that press on the suture threads 23 effecting the perfect securing of the same and also preventing that these threads become tangled together. The clamp or clip 24 will have spring means or the like which tend to close the same and will have gripping ends 26 formed adequately for the easy handling thereof. The tubes enveloping the branches 25 not only have the task of pressing on the threads 23, but also that of preventing the deterioration of the clamping thereof.

As has been said, two of the groups of threads 23 will run through the grooved sections 9 and the threads of each group will be held by a clamp 24, while the third group of suture threads will run through the center and will be likewise held by another clamp 24 in order to prevent the tangling thereof.

I claim:

1. A support for a cardiac valvular prosthesis to be implanted in a patient and to be secured to one branch of a sternal separator placed on the patient, said support comprising:

a substantially C-shaped section having spaced top and bottom branches for receiving the one branch of the sternal separator therebetween;

an immobilizing screw for securing the one branch in said C-shaped section;

a tube projecting from said top branch of said C-shaped section;

a rod positioned telescopically in said tube for longitudinal and rotational movement relative thereto;

a radial screw supported on said tube for immobilizing said rod in a selected position in said tube;

a U-shaped section having a middle branch extending transverse to said rod and rotatably supported at a free end of said rod;

two grooved members linked to end branches of said U-shaped section, respectively, for guiding suture threads;

a ferrule mounted on each of said two grooved sections at the ends thereof remote from said middle branch;

a tubular member rotatably supported in said ferrule; and a rod member extending transversely through said tubular member, rotatable and displaceable upward and downward therein, and having a downward end for supporting the cardiac valvular prosthesis.

2. A support according to claim 1 further comprising screw means supported on said middle branch for immobilizing said U-shaped section on the free end of said rod in a selected rotational position of said U-shaped section.

3. A support according to claim 2, further comprising a first side screw for immobilizing said tubular member and a second side screw for immobilizing said rod member in said tubular member.

4. A support according to claim 1, wherein said downward end of said rod member has a threaded portion, said support further comprising a middle piece having at one end thereof threaded means complementary to said threaded portion of said rod member for attaching said middle piece thereto and a threaded section at the other end thereof for connection to a rotator connected with the cardiac valvular prosthesis.

5. A support according to claim 1, wherein said two grooved members for guiding suture threads are widened towards said middle branch.

6. A support according to claim 5, further comprising a clamp having spaced clamping branches with plastic enveloping tubes for pressing the suture threads coming out of a respective groove member to prevent tangling of the suture threads.

* * * * *